(12) United States Patent
Osorio

(10) Patent No.: US 12,023,169 B2
(45) Date of Patent: Jul. 2, 2024

(54) CONTIGENT ACQUISITION AND ANALYSIS OF BIOLOGICAL SIGNAL OR FEATURE THEREOF FOR EPILEPTIC EVENT DETECTION

(71) Applicant: Flint Hills Scientific, L.L.C., Lawrence, KS (US)

(72) Inventor: Ivan Osorio, Leawood, KS (US)

(73) Assignee: FLINT HILLS SCIENTIFIC, L.L.C., Lawrence, KS (US)

( * ) Notice: Subject to any disclaimer, the term of this patent is extended or adjusted under 35 U.S.C. 154(b) by 1042 days.

(21) Appl. No.: 14/205,164

(22) Filed: Mar. 11, 2014

(65) Prior Publication Data
US 2014/0276129 A1   Sep. 18, 2014

Related U.S. Application Data

(60) Provisional application No. 61/799,953, filed on Mar. 15, 2013.

(51) Int. Cl.
*A61B 5/00* (2006.01)
*A61B 5/316* (2021.01)
*A61B 5/11* (2006.01)

(52) U.S. Cl.
CPC ........... *A61B 5/4094* (2013.01); *A61B 5/316* (2021.01); *A61B 5/1117* (2013.01)

(58) Field of Classification Search
None
See application file for complete search history.

(56) References Cited

U.S. PATENT DOCUMENTS

| | | | | |
|---|---|---|---|---|
| 2003/0236474 A1* | 12/2003 | Singh | ............... | A61B 5/4094 600/595 |
| 2006/0111644 A1* | 5/2006 | Guttag | ............... | A61B 5/048 600/544 |
| 2007/0150025 A1* | 6/2007 | Dilorenzo | ............... | G16H 50/30 607/45 |
| 2008/0161712 A1* | 7/2008 | Leyde | ............... | A61B 5/0006 600/544 |
| 2008/0269631 A1* | 10/2008 | Denison | ............... | A61B 5/0478 600/544 |
| 2009/0171168 A1* | 7/2009 | Leyde | ............... | A61B 5/291 600/301 |
| 2011/0251468 A1* | 10/2011 | Osorio | ............... | A61B 5/0476 600/300 |
| 2012/0046711 A1* | 2/2012 | Osorio | ............... | A61N 1/36114 607/45 |

* cited by examiner

*Primary Examiner* — Michael R Bloch
(74) *Attorney, Agent, or Firm* — CP3; Stephen Eisenmann

(57) ABSTRACT

We report a method comprising receiving a first indication to gather a first biological signal or feature thereof from a patient; gathering the first biological signal or feature thereof; receiving a second indication to stop gathering the first biological signal or feature thereof, wherein the second indication relates to a detection of an end of a brain state change; and stopping gathering the first biological signal or feature thereof. We also report a medical device system configured to implement the method. We also report a non-transitory computer readable program storage unit encoded with instructions that, when executed by a computer, perform the method.

7 Claims, 9 Drawing Sheets

CONTIGENT ACQUISITION AND ANALYSIS OF BIOLOGICAL SIGNAL OR FEATURE THEREOF FOR EPILEPTIC EVENT DETECTION

CROSS-REFERENCE TO RELATED APPLICATIONS

This application claims priority to U.S. Provisional Application Ser. No. 61/799,953, filed Mar. 15, 2013.

FIELD OF THE INVENTION

This disclosure relates to medical device systems and methods capable of detecting epileptic seizures.

SUMMARY OF THE INVENTION

In some embodiments, the present disclosure relates to a method, comprising: receiving a first indication to gather a first biological signal or feature thereof from a patient; gathering the first biological signal or feature thereof; receiving a second indication to stop gathering the first biological signal or feature thereof, wherein the second indication relates to a detection of an end of a brain state change; and stopping gathering the first biological signal or feature thereof.

In some embodiments, the present disclosure relates to a method, comprising: sensing a first biological signal or feature thereof with a first sensor; recording the first biological signal or feature thereof; sensing a second biological signal or feature thereof with a second sensor; recording the second biological signal or feature thereof; buffering the second biological signal or feature thereof to a memory buffer; analyzing the first biological signal or feature thereof to determine at least one feature; detecting a brain state change based on the at least one feature of the first biological signal or feature thereof; initiating analysis of the second biological signal or feature thereof in response to detecting the brain state change; confirming or not confirming the brain state change based on the analysis of the second biological signal or feature thereof; detecting an end of the brain state change based on at least one of the first biological signal or feature thereof or the second biological signal or feature thereof; and stopping analysis of the second biological signal or feature thereof based on detecting the end of the seizure.

In some embodiments, the present disclosure relates to a method, comprising: sensing a first biological signal or feature thereof with a first sensor; analyzing the first biological signal or feature thereof to determine at least one change in said signal or feature thereof; detecting a possible brain state change based on the at least one change of the first biological signal or feature thereof, wherein the detecting comprises comparing the signal or feature thereof to a reference value; initiating at least one responsive action comprising analyzing a second biological signal or feature thereof in response to the detecting; and confirming or not confirming the possible brain state change based on the analyzing the second biological signal or feature thereof.

In some embodiments, the present disclosure relates to a method, comprising: gathering a first biological signal or feature thereof from a patient; receiving an indication to gather a second biological signal or feature thereof from the patient; gathering the second biological signal or feature thereof; determining at least one of a sensitivity, a specificity, or a speed of detection of a pathological state in the patient from both the first biological signal or feature thereof and the second biological signal or feature thereof; continuing gathering of the biological signal or feature thereof having a better sensitivity of detection, a better specificity of detection, or a better speed of detection; and stopping gathering of the biological signal or feature thereof having a poorer sensitivity of detection, a poorer specificity of detection, or a poorer speed of detection.

In other embodiments, the present disclosure relates to a medical device system, comprising a first sensor configured to sense a first biological signal or feature thereof from a patient; a first signal or feature thereof recorder module configured to record the first biological signal or feature thereof; a first signal or feature thereof analysis module configured to analyze the first biological signal or feature thereof; a controller configured to generate a first indication based on biological signal or feature thereof to activate at least one of a second sensor, the second signal or feature thereof recorder module, or the second signal or feature thereof analysis module, such that all of the second sensor, the second signal or feature thereof recorder module, and the second signal or feature thereof analysis module are activated and to generate a second indication based on the second biological signal or feature thereof to deactivate at least one of the first sensor, the first signal or feature thereof recorder module, or the second signal or feature thereof analysis module; and a memory configured to store at least the first analyzed biological signal or feature thereof.

In some embodiments, the present disclosure relates to a non-transitory computer readable program storage unit encoded with instructions that, when executed by a computer, perform a method as described above.

BRIEF DESCRIPTION OF THE DRAWINGS

The disclosure may be understood by reference to the following description taken in conjunction with the accompanying drawings, in which like reference numerals identify like elements, and in which.

Figure 1:
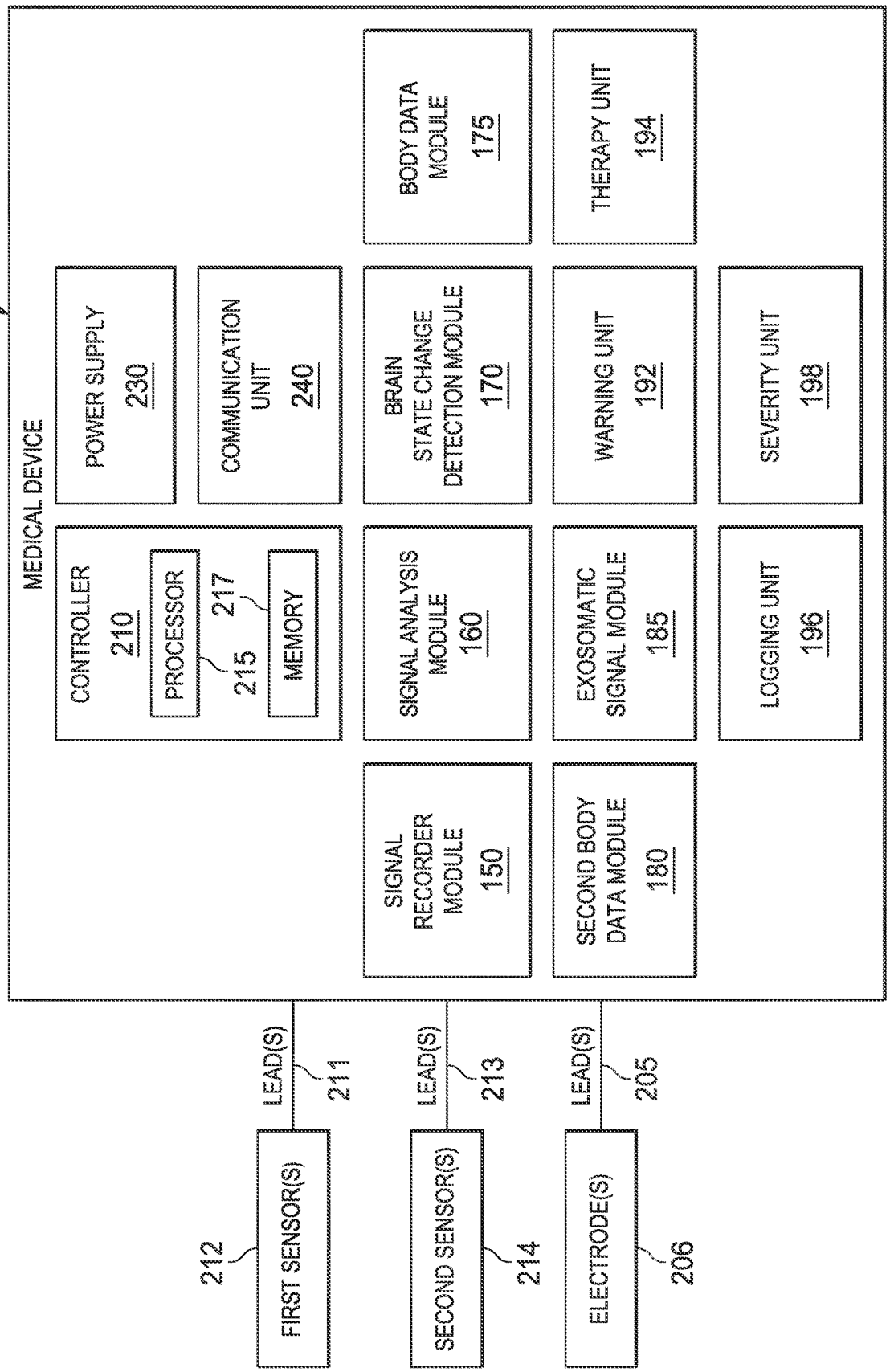
FIG. 1 shows a schematic diagram of a medical device system, in accordance with some embodiments of the present disclosure.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

DETAILED DESCRIPTION OF SPECIFIC EMBODIMENTS

Illustrative embodiments of the disclosure are described herein. For clarity, not all features of an actual implementation are described. In the development of any actual embodiment, numerous implementation-specific decisions must be made to achieve design-specific goals, which will vary from one implementation to another. Such a development effort, while possibly complex and time-consuming, would nevertheless be a routine undertaking for persons of ordinary skill in the art having the benefit of this disclosure.

More information regarding testing of a patient's responsiveness and/or awareness may be found in other patent applications assigned to Flint Hills Scientific, L.L.C. or Cyberonics, Inc., such as, U.S. Ser. No. 12/756,065, filed Mar. 7, 2010. Any patent application identified in this paragraph is hereby incorporated herein by reference.

More information regarding detecting an epileptic event from cardiac data, as well as information regarding measures of central tendency that can be determined from time series of body data, may be found in other patent applications assigned to Flint Hills Scientific, L.L.C. or Cyberonics, Inc., such as, U.S. Ser. No. 12/770,562, filed Apr. 29, 2010; U.S. Ser. No. 12/771,727, filed Apr. 30, 2010; U.S. Ser. No. 12/771,783, filed Apr. 30, 2010; U.S. Ser. No. 12/884,051, filed Sep. 16, 2010; U.S. Ser. No. 13/554,367, filed Jul. 20, 2012; U.S. Ser. No. 13/554,694, filed Jul. 20, 2012; U.S. Ser. No. 13/559,116, filed Jul. 26, 2012; and U.S. Ser. No. 13/598,339, filed Aug. 29, 2012. Each of the patent applications identified in this paragraph is hereby incorporated herein by reference.

More information regarding detecting an epileptic event from multiple body data types, and examples of such body data types, may be found in other patent applications assigned to Flint Hills Scientific, L.L.C. or Cyberonics, Inc., such as, U.S. Ser. No. 12/896,525, filed Oct. 1, 2010, now U.S. Pat. No. 8,337,404, issued Dec. 25, 2012; U.S. Ser. No. 13/098,262, filed Apr. 29, 2011; U.S. Ser. No. 13/288,886, filed Nov. 3, 2011; U.S. Ser. No. 13/554,367, filed Jul. 20, 2012; U.S. Ser. No. 13/554,694, filed Jul. 20, 2012; U.S. Ser. No. 13/559,116, filed Jul. 26, 2012; and U.S. Ser. No. 13/598,339, filed Aug. 29, 2012. Each of the patent applications identified in this paragraph is hereby incorporated herein by reference.

More information regarding automated assessments of disease states, comorbidities, and the like may be found in other patent applications assigned to Flint Hills Scientific, L.L.C. or Cyberonics, Inc., such as, U.S. Ser. No. 12/816,348, filed Jun. 15, 2010; and U.S. Ser. No. 12/816,357, filed Jun. 15, 2010. Each of the patent applications identified in this paragraph is hereby incorporated herein by reference.

More information regarding detection, assessment, and management of extreme disease states, such as extreme epileptic events, may be found in other patent applications assigned to Flint Hills Scientific, L.L.C. or Cyberonics, Inc., such as, U.S. Ser. No. 13/040,996, filed Mar. 4, 2011; U.S. Ser. No. 13/091,033, filed Apr. 20, 2011; U.S. Ser. No. 13/472,365, filed May 15, 2012; and U.S. Ser. No. 13/333,235, filed Dec. 21, 2011. Each of the patent applications identified in this paragraph is hereby incorporated herein by reference.

More information regarding the detection of brain or body activity using sensors implanted in proximity to the base of the skull may be found in other patent applications assigned to Flint Hills Scientific, L.L.C. or Cyberonics, Inc., such as, U.S. Ser. No. 13/678,339, filed Nov. 15, 2012. Any patent application identified in this paragraph is hereby incorporated herein by reference.

Biological signals generated by organs other than the brain (referred to hereinafter as extracerebral signals) are less specific and less sensitive for the detection of epileptic seizures than those originating from the cerebral cortex. To address this limitation, and to make extracerebral detection comparable in clinical utility to cortical signals, acquisition, processing and analysis of more than one extracerebral signal may be required. Since this strategy may negate (at least in part) the computational cost saving inherent in extracerebral signals, the present disclosure provides an approach whereby a second signal is acquired, processed, or analyzed in response to certain cues such as a detection of a pathological state (e.g., a seizure). The present approach may this be considered as a contingent approach to processing some signals.

Some embodiments herein provide for performing an acquisition and/or analysis of a biological signal of a patient in response to a detected event. In one embodiment, the detected event may be a detection of a brain state change (e.g., an epileptic seizure). The detection of the brain state change may be performed by acquiring and analyzing a different biological signal of the patient from that on which the detection was based. For example, a detection of a brain state change may be performed by acquiring and analyzing a respiratory signal of a patient. Upon detection of the brain state change, another biological signal, e.g., a cardiac signal, may be acquired. Further analysis of the brain state change may then be performed.

More specifically, in some embodiments, acquisition of at least a second biological signal, which may be triggered by the detection of a brain state change based upon a first biological signal, may be used to perform a confirmation process. The second biological signal may be analyzed to determine whether to confirm or deny the detection of the brain state change, or to assess therapeutic efficacy. In other embodiments, in addition to the confirmation process, the second biological signal may be analyzed to determine the type and severity of the brain state change. Still further, in other embodiments, the second biological signal may be analyzed to determine the type of responsive action to be taken, e.g., type of notification and/or treatment.

Embodiments herein provide for increasing the efficiency of signal processing and analysis, improving the detection of state changes, and decreasing the processor burden of a medical device for predicting, detecting and/or treating an epileptic event. For example, the first biological signal may be a signal that is relatively easy to acquire and analyze. For example, a heart rate detector may be used to acquire the heart rate of the patient. The heart rate may then be compared to a threshold heart rate. If the detected heart rate crosses the threshold, a second biological signal, such as respiratory signal or a more complex cardiac signal, such as the heart rate variability (HRV) or EKG morphology, may be acquired and analyzed. The second biological signal may then be used to predict, detect, quantify or treat an epileptic event, or assess the efficacy or adverse effects of a therapy. In some examples, acquiring the second biological signal may be more computationally costly. Accordingly, acquisition and analysis of the second biological signal may be performed only when triggered by the first biological signal, which reduces the processor and/or computational burden on the medical device.

In some embodiments, low complexity/computationally inexpensive signals may be used as "sentinel" signals that are used to trigger or "summon" other signals when needed. This may provide for smaller devices, smaller batteries, and/or longer life—which may be significant factors in determining whether an implantable medical device may be commercially viable. In this manner, more efficient and cost-effective prediction, detection, and/or treatment of pathological events (e.g., an epileptic seizure) may be provided.

FIG. 1 shows a schematic representation of a medical device system, according to some embodiments of the present disclosure. The medical device system 100 may comprise a medical device 200, first sensor(s) 212, lead(s) 211 coupling the first sensor(s) 212 to the medical device 200, second sensor(s) 214, and lead(s) 213 coupling the second sensor(s) 214 to the medical device 200. The sensors 212 are capable of detecting a variety of biological signals of the patient, such as autonomic signals, neurological signals, endocrine signals, metabolic signals, tissue stress signals, etc. Further, the medical system 100 may also comprise one or more electrodes 206 for delivering electrical signal therapy to a portion of the patient's body, e.g., the vagus nerve. Therapeutic electrical signals may be sent from the medical device 200 to the electrodes 206 via lead(s) 205.

Various components of the medical device 200, such as controller 210, processor 215, memory 217, power supply 230, communication unit 240, warning unit 192, therapy unit 194, logging unit 196, and severity unit 198 have been described in other patent applications assigned to Flint Hills Scientific, LLC or Cyberonics, Inc., such as those incorporated by reference, supra.

The medical device 200 may comprise a signal recorder module 150 configured to record a first biological signal or a feature of the first biological signal, e.g., a signal or feature thereof collected from sensor(s) 212 or 214. The signal recorder module 150 may receive directly from the sensors 212, 214, or alternatively, from a body data module 175, which is capable of receiving and processing a plurality of biological signals. The body data module 175 is described in further details below. The signal recorder module 150 is capable of storing analog and/or digital body signals. In some embodiments, the signal recorder module 150 is capable of correlating, stacking, and organizing data for orderly recovery and statistical analysis. In one embodiment multiple signal recording modules may be utilized, while in other embodiments a single signal recorder is endowed with multiplexing capacity. In one embodiment, multiple signals may be contingently multiplexed through one module. In another embodiment, signals may be prioritized for multiplexing based on certain metrics (e.g., sensitivity, specificity, and/or speed of detection). As part of contingent multiplexing or prioritizing multiplexing, signals may be added or removed from a filter bank.

The medical device 200 may comprise a signal analysis module 160 configured to analyze biological signals or features thereof "Analyze" here may include processing of raw recorded signals or features thereof (e.g., filtering, amplifying, etc.) to yield processed signals or features thereof, and/or the performance of one or more calculations on the processed signals or features thereof to yield informative data. For example, if the first biological signal or feature thereof is an electrocardiography (EKG) signal or feature thereof, the signal or feature thereof may be processed, then calculations may be performed to determine the patient's heart rate e.g., R-R intervals from the EKG signal or feature thereof.

In some embodiments, the signal analysis module 160 may be configured to determine a first feature of the first biological signal or feature thereof, wherein the first feature is one of power in certain frequency band, a rhythmicity index, a waveform morphology, a synchronization level, a direction of a movement, an amplitude of a movement or an acceleration of a movement.

Recording, processing, and performing calculations on a signal or feature thereof may together be referred to as "gathering" a signal or feature thereof. As should be apparent, all of the first sensor, the signal or feature thereof recorder module, and the signal or feature thereof analysis module should be activated if it is desired to gather a signal or feature thereof collectable by the first sensor.

In some embodiments, the first biological signal or feature thereof is an electroencephalography (EEG) signal or feature thereof, an electrocorticography (ECoG) signal or feature thereof, an EKG signal or feature thereof, a kinetic signal or feature thereof, a reaction time signal or feature thereof, an awareness signal or feature thereof, or a responsiveness signal or feature thereof.

In some embodiments, the first biological signal or feature thereof is an electrocardiography (EKG) signal or feature thereof and the signal or feature thereof analysis module is configured to determine a first feature of the first biological signal or feature thereof, wherein the first feature is one of heart rate, heart rate variability, EKG morphology, heart rhythm, or Q-T interval.

The controller 210 may be configured to generate a first indication based at least in part on a second biological signal or feature thereof (such as may be provided by second body data module 180, described below) to activate at least one of the first sensor, the signal or feature thereof recorder module, or the signal or feature thereof analysis module, such that all of the first sensor, the signal or feature thereof recorder module, and the signal or feature thereof analysis module are activated.

In some embodiments, the second biological signal or feature thereof may be an electrocardiography (EKG) signal or feature thereof. In one embodiment, the first biological signal may be a cardiac signal (EKG) and the second signal may be a cortical signal (ECoG). As used herein, the first biological signal generally refers to a signal which is most being used as the sentinel signal to trigger the recording of the second signal, while the second biological signal refers to a signal which is contingently acquired based on the first signal.

Alternatively or in addition, the controller 210 may be configured to generate at least one of the first indication or the second indication, based at least in part on at least one exosomatic signal received via an exosomatic signal module 185 or feature thereof. In some embodiments, the at least one exosomatic signal or feature thereof may be a time of day signal or feature thereof, a time of month signal or feature thereof, a luminance level signal or feature thereof, an acoustic noise level signal or feature thereof, a temperature signal or feature thereof, a barometric pressure signal or feature thereof, a signal or feature thereof indicative of a physical activity of the patient and when it was performed by the patient, a signal or feature thereof indicative of an attention level of the patient and when the patient was attentive, a signal or feature thereof indicative of a cognitive activity of the patient, the type of cognitive activity and when it was performed by the patient, a signal or feature thereof indicative of a time elapsed since the last seizure of the patient, the last seizure type or class, the last seizure severity of the patient, a signal or feature thereof indicative of a time elapsed since the delivery of a therapy to the patient, the type of therapy and its dose or parameters, the efficacy of the therapy, delivered to the patient, the adverse effects of the therapy and their type and severity, or a signal or feature thereof indicative of a time elapsed since the last caloric intake and its amount, a signal or feature thereof indicative of stress level and when it changes of the patient.

The controller 210 may also be configured to generate a second indication based on the second biological signal or feature thereof to deactivate at least one of the first sensor, the signal or feature thereof recorder module, or the signal or feature thereof analysis module. By doing so, the first biological signal or feature thereof would not be gathered/acquired.

In some embodiments, the first indication is based on a seizure event onset determined from the second biological signal or feature thereof, and the second indication is based on a seizure event end determined from the second biological signal or feature thereof ("End" here refers to the return of a body data series indicative of the seizure returning to baseline, either spontaneously or in response to applied therapy. A seizure end in response to applied therapy may be termed a "termination"). The seizure event onset and seizure event end may be determined by a brain state change detection module 170.

The brain state change detection module 170 may be configured to detect a brain state change, based at least in part on a biological signal or feature thereof, such as the first biological signal, or feature thereof, the second biological signal or feature thereof, or both. In some embodiments, the brain state change is an epileptic event, such as a seizure. The brain state change detection module 170 is capable of detecting electrical, and/or chemical changes relating to a portion of a patient's brain by analyzing body data indicative of the state of the patient's brain.

In one embodiment, the brain state change detection module 170 may be configured to detect a brain state change based on the first biological signal or feature thereof, and may be configured to detect the end of the brain state change based on the second biological signal or feature thereof. Alternatively or in addition, the brain state change detection module 170 may be configured to use the second biological signal or feature thereof to provide a secondary analysis regarding brain state changes, e.g., to determine if false positive/false negative performance of brain state change detections made by the brain state change detection module 170 based on the first biological signal or feature thereof is satisfactory, by using the second biological signal or feature thereof.

Alternatively or in addition, the brain state change detection module 170 may be configured to provide a first indication usable by one or more of the units 192-198 to warn, deliver a therapy, determine a severity, and/or log the occurrence of a brain state change, based on the first biological signal or feature thereof, and to provide a second indication usable by one or more of the units 192-198 to terminate or rescind a warning, terminate or rescind delivery of a therapy, terminate determining a severity, and/or terminate or rescind logging the occurrence of a brain state change, based on the second biological signal or feature thereof. The memory 217 may be configured to store at least the first and/or the second analyzed biological signals or features thereof.

The medical device 200 may further comprise a body data module 175, configured to gather a plurality of biological signals or features thereof and provide it or data based on it to other elements, e.g., brain state change detection module 170.

Figure 2:
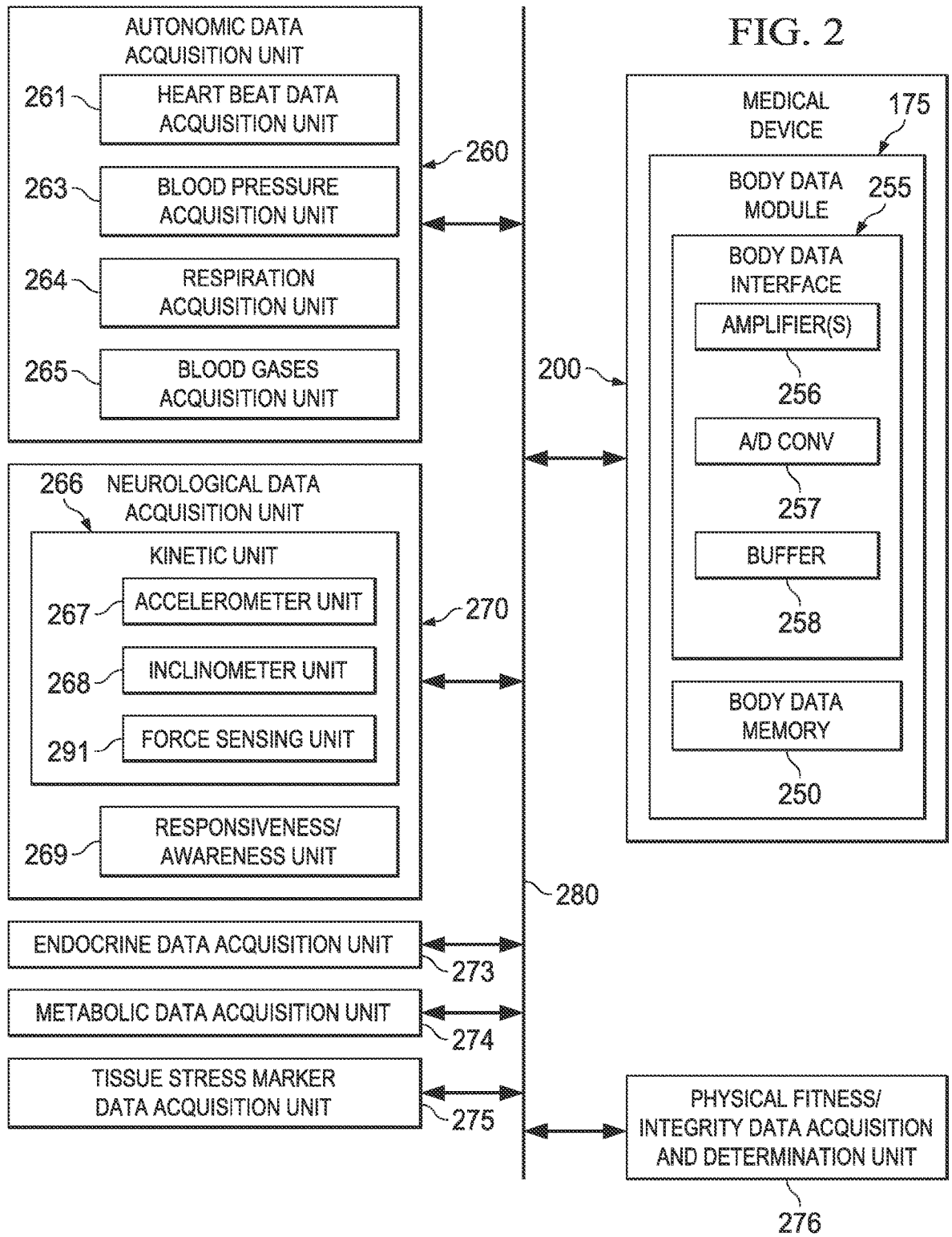
FIG. 2 shows a schematic diagram of data acquisition components of a medical device system, in accordance with some embodiments of the present disclosure.

FIG. 2 shows data acquisition elements of the medical device system 100 in more detail. FIG. 2 depicts an exemplary implementation of the body data module 175 described above with respect to FIG. 1. The body data module 175 may include a body data memory 250 for storing and/or buffering data in the body data collection module 175. The body data memory 250 may, in some embodiments, be adapted to store body data for logging or reporting purposes and/or for future body data processing. The body data collection module 175 may also include one or more body data interfaces 255. The body data interface 255 may provide an interface for input/output (I/O) communications between the body data module 175 and body data acquisition units/modules (e.g., [260-270], [273-276]) via connection 280. Connection 280 may a wired or wireless connection, or a combination of the two. The connection 280 may be a bus-like implementation or may include an individual connection (not shown) for each, or some number, of the body data acquisition units (e.g., [260-270], [273-276]). The connection 280 may also include connection elements as would be known to one of skill in the art having the benefit of this disclosure. The specific implementation of the connection 280 does not serve to limit other aspects of various embodiments described herein unless specifically described. In various embodiments, the body data acquisition units may include, but are not limited to, an autonomic data acquisition unit 260, a neurologic data acquisition unit 270, and endocrine data acquisition unit 273, a metabolic data acquisition unit 274 and/or a tissue stress marker data acquisition unit 275. In one embodiment, the body data units may include a physical fitness determination unit 276. In one embodiment, the autonomic data acquisition unit 260 may include a heart beat data acquisition unit 261 adapted to acquire heart sounds, EKG data, PKG data, heart echo, apexcardiography and/or the like, a blood pressure acquisition unit 263, a respiration acquisition unit 264, a blood gases acquisition unit 265, and/or the like. In one embodiment, the neurologic data acquisition unit 270 may contain a kinetic unit 266 that may comprise an accelerometer unit 267, an inclinometer unit 268, and/or the like; the neurologic data acquisition unit 270 may also contain a responsiveness/awareness unit 269 that may be used to determine a patient's responsiveness to testing/stimuli and/or a patient's awareness of their surroundings. These lists are not inclusive, and the body data module 175 may collect additional data not listed herein, that would become apparent to one of skill in the art having the benefit of this disclosure. The body data acquisition units ([260-270], [273-276]) may be adapted to collect, acquire, receive and/or transmit heart beat data, EKG data, PKG data, heart echo, apexcardiography, heart sound data, blood pressure data, respiration data, blood gases data, body acceleration data, body incline data and/or the like. In one embodiment, the neurological data acquisition unit 266 includes a force sensing unit 291.

The body data interface(s) 255 may include various amplifier(s) 256, one or more A/D converters 257 and/or one or more buffers 258 or other memory (not shown). In one embodiment, the amplifier(s) 256 may be adapted to boost incoming and/or outgoing signal strengths for signals such as those to/from any body data acquisition units/modules (e.g., ([260-270], [273-276]) or signals to/from other units/modules of the medical device 200. The A/D converter(s)

257 may be adapted to convert analog input signals from body data acquisition unit(s)/module(s) (e.g., ([260-270], [273-276]) into a digital signal or feature thereof format for processing by controller 210 (and/or processor 215). Such analog signals may include, but are not limited to, heart beat data, EKG data, PKG data, heart echo, apexcardiography, heart sound data, blood pressure data, respiration data, blood gases data, body acceleration data, body incline data, and/or the like. A converted signal or feature thereof may also be stored in a buffer(s) 258, a body data memory 250, or some other memory internal to the medical device 200 (e.g., memory 217) or external to the medical device 200 (e.g., one or more of a monitoring unit, a local database unit, a remote database unit, or a remote device, among others (not shown)). The buffer(s) 240 may be adapted to buffer and/or store signals received by the body data module 175 as well as signals to be transmitted by the body data module 175. In various embodiments, the buffer(s) 258 may also be adapted to buffer and/or store signals in the body data-module 175 as these signals are transmitted between components of the body data-module 175.

Figure 3:
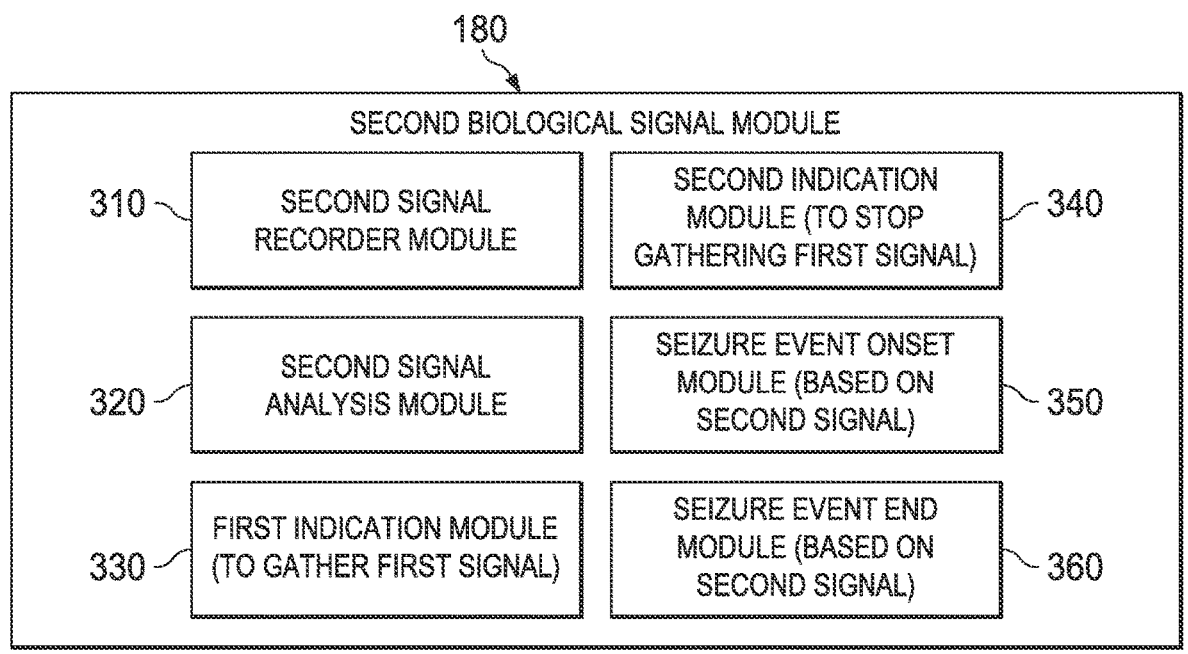
FIG. 3 shows a schematic diagram of a second biological signal or feature thereof module, according to some embodiments of the present disclosure.

FIG. 3 shows a schematic representation of the second body data module 180 according to some embodiments of the present disclosure. The second body data module 180 may comprise a second signal or feature thereof recorder module 310 and a second signal or feature thereof analysis module 320 to perform various signal or feature thereof gathering tasks, analogously to the signal or feature thereof recorder module 150 and the signal analysis module 160 described above.

The second body data module 180 may comprise a first indication module 330 configured to make use of data provided by the signal or feature thereof gathering elements 310 and 320 to provide an indication to gather the first signal or feature thereof. Similarly, the second body data module 180 may comprise a second indication module 340 to provide an indication to stop gathering the first signal or feature thereof.

The second body data module 180 may comprise a seizure event onset module 350 configured to make use of data provided by the signal or feature thereof gathering elements 310-320 to detect a seizure onset. The detected seizure onset may be used by the first indication module 330 in determining whether to provide the first indication to gather the first signal or feature thereof. Similarly, the second body data module 180 may comprise a seizure event end module 360 configured to detect a seizure end. The detected seizure end may be used by the second indication module 340 in determining whether to provide the second indication to stop gathering the first signal or feature thereof.

In some embodiments, the medical device system may comprise a first sensor configured to sense a first biological signal or feature thereof from a patient; a signal or feature thereof recorder module configured to record the first biological signal or feature thereof; a signal or feature thereof analysis module configured to analyze the first biological signal or feature thereof; a detection module configured to generate a first indication of a brain state change based on said first biological signal or feature thereof; a controller module configured to activate at least one of a second sensor configured to sense a second biological signal or feature thereof recorder module in response to a change in the first signal or feature thereof, a second signal or feature thereof analysis module, a second indication of a brain state change based on a change in the second biological signal or feature thereof; and a responsive action based on the concordance or discordance of said first and second signal or their features thereof, said action consisting of deactivation of at least one of the first sensor, the signal or feature thereof recorder module, or the signal or feature thereof analysis module; and a memory configured to store at least the first analyzed biological signal or feature thereof.

In some embodiments, the present disclosure relates to a method, comprising: sensing a first biological signal or feature thereof with a first sensor; recording the first biological signal or feature thereof; analyzing the first biological signal or feature thereof to determine at least one feature; detecting a brain state change based on the at least one feature of the first biological signal or feature thereof; sensing a second biological signal or feature thereof with a second sensor in response to said detection of a brain state change; recording the second biological signal or feature thereof in response to said detection of a brain state change; initiating analysis of the second biological signal or feature thereof in response to detecting the brain state change; confirming or not confirming the brain state change based on the analysis of the second biological signal or feature thereof; detecting an end of the brain state change based on at least one of the first biological signal or feature thereof or the second biological signal or feature thereof; and stopping analysis of the second biological signal or feature thereof based on detecting the end of the seizure.

Figure 4:
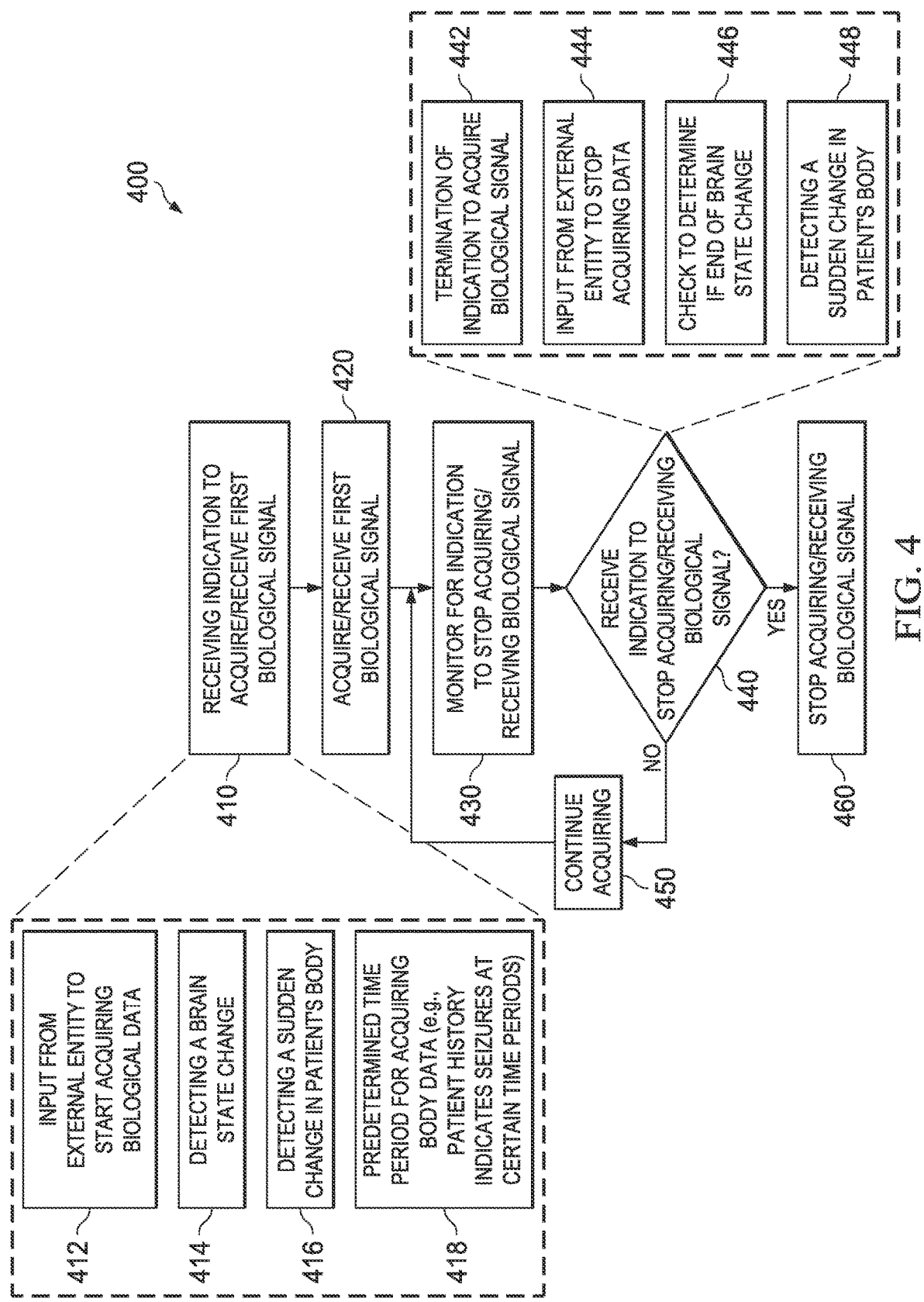
FIG. 4 shows a flowchart depiction of a method, according to some embodiments of the present disclosure.

Turning now to FIG. 4, a flowchart depiction of a method 400 of performing a contingent acquisition of biological signal(s), in accordance with one embodiment, is illustrated. The medical device 200 may receive an indication to acquire or receive a first biological signal (block 410). The indication to acquire a biological signal may be one of many types of prompts that may initiate acquisition of biological signals. For example, the indication may be an input from an external entity to start acquiring biological data (block 412). In some instances, the patient may feel a change in his or her body, wherein the change may be indicative of an occurrence of an epileptic event. As a result, the patient may provide an input to the medical device 200 indicating the change. The input may be a magnet swipe input, a tap sensor input, or an electronic input, wherein the input may initiate the acquisition of biological data.

In other embodiments, the indication to acquire biological data may be initiated by the detection of a brain state change (block 414). For example, the medical device 200 may detect an epileptic event based upon one or more detection methods, such detection based upon monitoring and analyzing one or more body data signals. For example, the heart rate may be monitored and analyzed to detect a possible a brain state change, which may trigger the acquisition of one or more additional biological signals. In this manner, a signal (e.g., heart rate) that is easy to acquire, has a high S/N or is computationally inexpensive to process, may be constantly monitored ("Sentinel" signal). Upon detecting a potential brain state change based upon a sudden change in the heart rate, further acquisition and analysis of another biological signal may be performed. Thereby, acquisition, processing and analysis of a biological signal that may have high complexity, low S/N or may be computationally expensive to process and analyze by the medical device 200 may only be contingently utilized in response to a certain cue (e.g., the onset of an epileptic event.) In this manner, more efficient use of the medical device 200, the battery, the processor, etc., of the medical device 200, may be realized while still performing efficient and cost-effective detection of one or more diseases in the patient's body.

Further, another example of communication that initiates the acquisition of a first biological data may be the detection of a sudden change in the patient's body (block 416). One of a number of sudden changes in the patient's body may be detected by the medical device 200. One example of a sudden change may be a sudden change in breathing, a detection by an accelerometer of a certain change in movement in the patient's body, a sudden change in an inclinometer output indicating a sudden shift in the position of the patient's body, etc. Based on the sudden change in the patient's body, the acquisition of more complex or more taxing acquisition of another biological signal may be performed.

Another example of an indication to acquire or receive the first biological signal may be a predetermined time period for acquiring body data (block 418). For example, a patient's history may indicate that certain epileptic events may occur at particular times for a patient; therefore, a pre-determined time may be determined by the medical device 200 to provide an automated indication to initiate acquisition and analysis of a biological signal. Those skilled in the art having benefit of the present disclosure, will appreciate that other types of indications may be provided to the medical device 200 for initiating the acquisition and/or analysis of biological signal, and still remain within the scope and spirit of the present embodiments.

Upon receiving indication to acquire or receive a first biological signal, the medical device 200 may begin acquisition and/or receiving of the first biological signal (block 420). In some examples sensors operatively coupled to the medical device 200 may be utilized to acquire the biological signals. In other embodiments, external devices may acquire and provide the biological signals to the medical device 200. In some embodiments, the biological signals may be processed and analyzed by the medical device 200 for performing proper detection, predictions, or other analysis. In other embodiments, the acquired or received biological signals may be stored and/or transmitted to an external entity for further analysis.

In some cases, the acquisition and receiving of the first biological signal may be relatively taxing on the resources of the medical device system 100. Therefore, efficient timing and limitation of the acquisition process may be desirable. As such, upon acquiring and receiving the first body signal, the medical device system 100 may monitor for an indication to stop the acquisition and/or receiving of the first biological signal (block 430). The medical device 200 may determine whether it has received an indication to stop the acquisition of the first biological signal (block 440). Upon a determination that no such indication has been received, the medical device system 200 may continue acquiring the first biological signal (block 450). Upon continuing the acquisition of the biological signal, the medical device 200 may continue to monitor for an indication to stop the acquisition, as indicated by the flow from block 440, to block 450, to block 430 and back to block 440. In some embodiments, the signal to stop or terminate receiving the first biological signal may occur in response to a determination to switch to a different first body signal for use as a fiducial in monitoring the patient's condition.

The indication to stop acquiring or receiving biological signal may be in one of several forms, as exemplified in FIG. 4 (blocks 442, 444, 446, and 448). In some embodiments, the indication to stop acquiring may take on the form of a termination of indication to acquire biological signals (block 442). For example, after the acquisition of the second signal is initiated, subsequent data may indicate that the acquisition of the signal is unnecessary, in which case the acquisition of the second signal may be terminated or stopped. For example, data (e.g., exosomatic data) may indicate that the probability of an epileptic brain state has become sufficiently low to merit termination of acquisition of the second signal. In other examples, a constant polling of a signal may be made to determine whether the indication to acquire data is still active. In other embodiments, a periodic signal may be sent to the medical device 200 indicating to continue acquisition of the biological data, and upon a missed periodic signal, an interpretation may be made that it was a termination of an indication to acquire biological signal.

Another example of an indication to stop acquisition may be an input from an external entity stop acquiring data (block 444). In some examples, the patient may provide an input to stop the acquisition upon feeling that the patient's body is functioning properly. Other external indications may be provided by from an external device, or manually from a medical professional. Another example of an indication to stop acquisition may be a check to determine if there is an end to the brain state change that initially had triggered the acquisition (block 446). Therefore, the detection and analysis of a brain state change may lead to determination of the indication to acquire biological signal. Further, upon a detection of a change or a return to a previous baseline state in the patient's body, an indication may be interpreted to have been received to stop acquisition (block 448). For example, if an inclinometer indicates that the patient is in a proper upright position for a predetermined period of time, an indication will be provided to stop the acquisition of biological signal. Other indications may include an accelerometer-reading indicating normal patient movement, which may trigger the termination of the acquisition of biological signal.

Upon determining that an indication to stop acquiring or receiving biological signal has been received (block 440), the medical device 200 may stop the acquisition and reception of the biological signal (block 460). In this manner, biological signal acquisition is contingent upon cues and occurs only when needed, and the acquisition may be terminated when the need is satisfied. Therefore, a more efficient operation of acquisition, analysis and termination of acquisition of body signals is provided by embodiments herein.

In one embodiment, signal acquisition or processing or analysis may be discontinued during periods or conditions/states associated with low probability of occurrence of pathological events (e.g., seizures). This may be implemented, for example, in monitoring patients with nocturnal frontal lobe epilepsy in whom the probability of having a seizure while awake is negligible. In another example at a different timescale, monitoring may occur only during the premenstrual period in women having catamenial epilepsy. In other patients, the monitoring may be discontinued when the patient is in a neuroprotected state, or when the safety or social risks to the patient associated with seizures are minimal.

Figure 5:
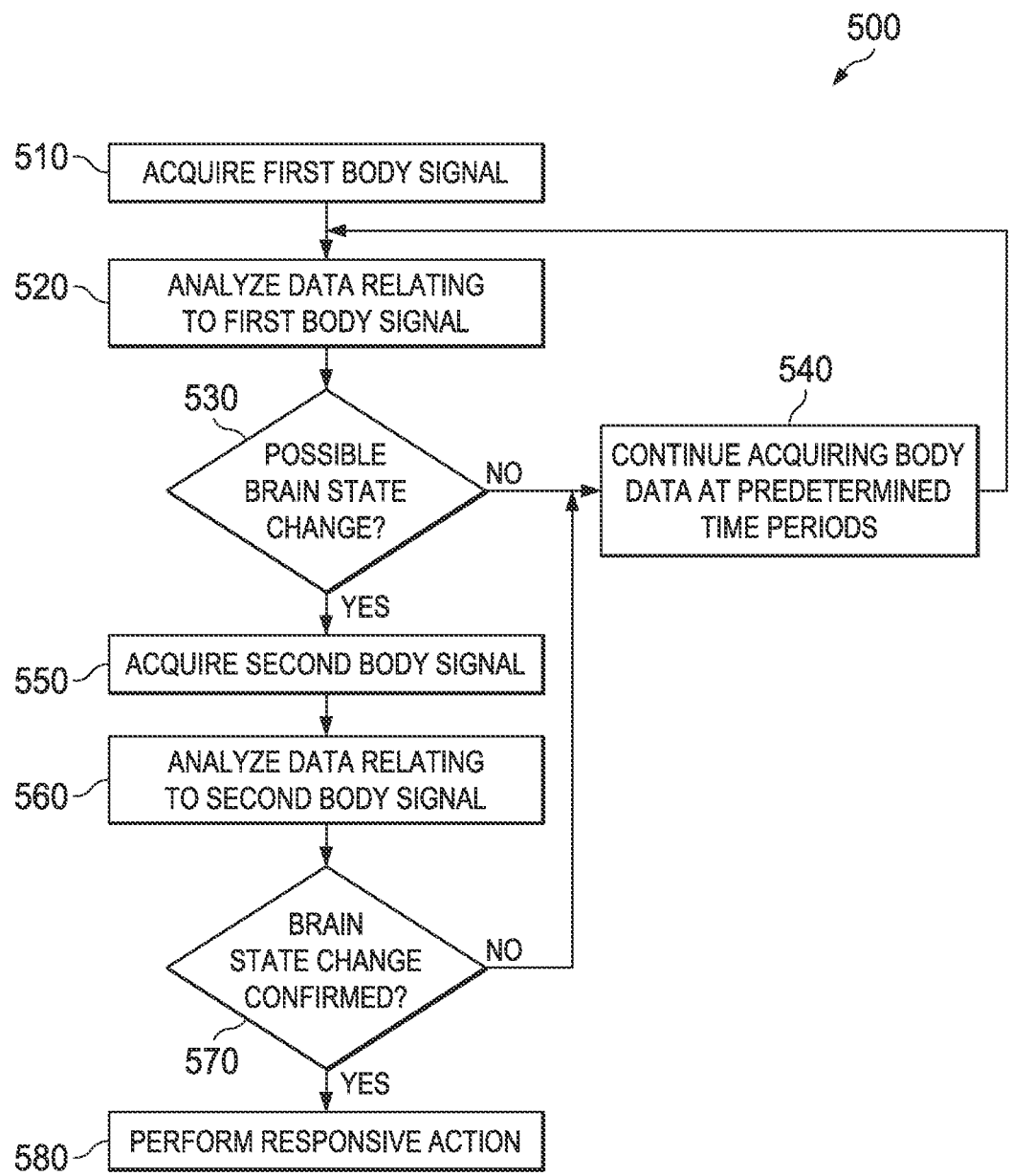
FIG. 5 shows a flowchart depiction of a method, according to some embodiments of the present disclosure.

Turning now to FIG. 5, a flowchart depiction of a method 500 for performing the contingent acquisition and/or recording of a body signal, in accordance with an alternative embodiment, is illustrated. The medical device 200 may acquire a first body signal (block 510). Upon acquisition of the first body signal, the medical device 200 may analyze the data relating to the first body signal (block 520). This analysis may comprise processing the first body signal, converting the first body signal into digital data, performing comparisons to reference or threshold values, and/or performing comparison to shapes of at least a portion of the body signal to reference shapes. Based upon analysis of the data relating to the first body signal, the medical device 200 may determine whether a possible brain state change exists (block 530). Possible brain state change may relate to one or more indications that a change in the patient's body has been detected and an impending epileptic event may be possible. Upon a determination that a possible brain state change has not been detected, the medical device 200 may continue acquiring body data at predetermined time periods (block 540). Subsequently, this data may be analyzed and a determination may be made whether there exists a possible brain state change (see flow from block 530, to 540, to 520 and back to 530). In some embodiments the first body signal may be a signal that can be acquired with relative ease and use of minimal resources of the medical device system 100. Therefore, a minimal use of computing resources and power may be utilized while monitoring the first body signal and performing analysis to detect a possible brain state change.

Upon a detection of a possible brain state change (block 530), acquisition or reception of a second body signal may be performed (block 550). In some embodiments the acquisition of the second body signal may involve acquiring more complex signals that may require greater in-depth analysis. Therefore, in some embodiments, this process may only be performed when triggered by the detection of a possible brain state change, thereby providing for efficient detection of an epileptic event.

Upon acquisition of the second body signal (block 550), data representative of that signal may be analyzed (block 560). The analysis of the data relating to the second body signal may comprise processing the second body signal and performing analysis. The analysis may include performing comparisons of features of the signal, including amplitude, frequency, morphology, etc.

The medical device 200 may then determine whether the brain state change is confirmed (block 570). That is, the analysis of the second body signal may be used to confirm the possible brain state change detected by the analysis of the first body signal. Therefore, the possible brain state change of block 530 may be confirmed as an actual brain state change, or may be denied (block 570). This determination may be based on the analysis performed on second body signal. Upon a determination that the brain state change has not been confirmed, the flow moves from block 570 to block 540, where the acquisition of body data may be continued at predetermined time periods.

Upon a determination that the brain state change is confirmed, a responsive action may be performed by the medical device system 100 (block 580). The responsive action may comprise one or more of providing a therapy, logging one or more data sets relating to the acquisition of the first and/or second body signals, as well as data relating to the comparison and the results of such comparisons described above. Further, the responsive action may include notifying one or more entities regarding the brain state change confirmation. In some embodiments, when a brain state change has not been confirmed (block 570), the acquisition of body signals may be suspended for a predetermined time period. In this manner, resources of the medical device system 100 are conserved when brain state changes are not present.

Figure 6:
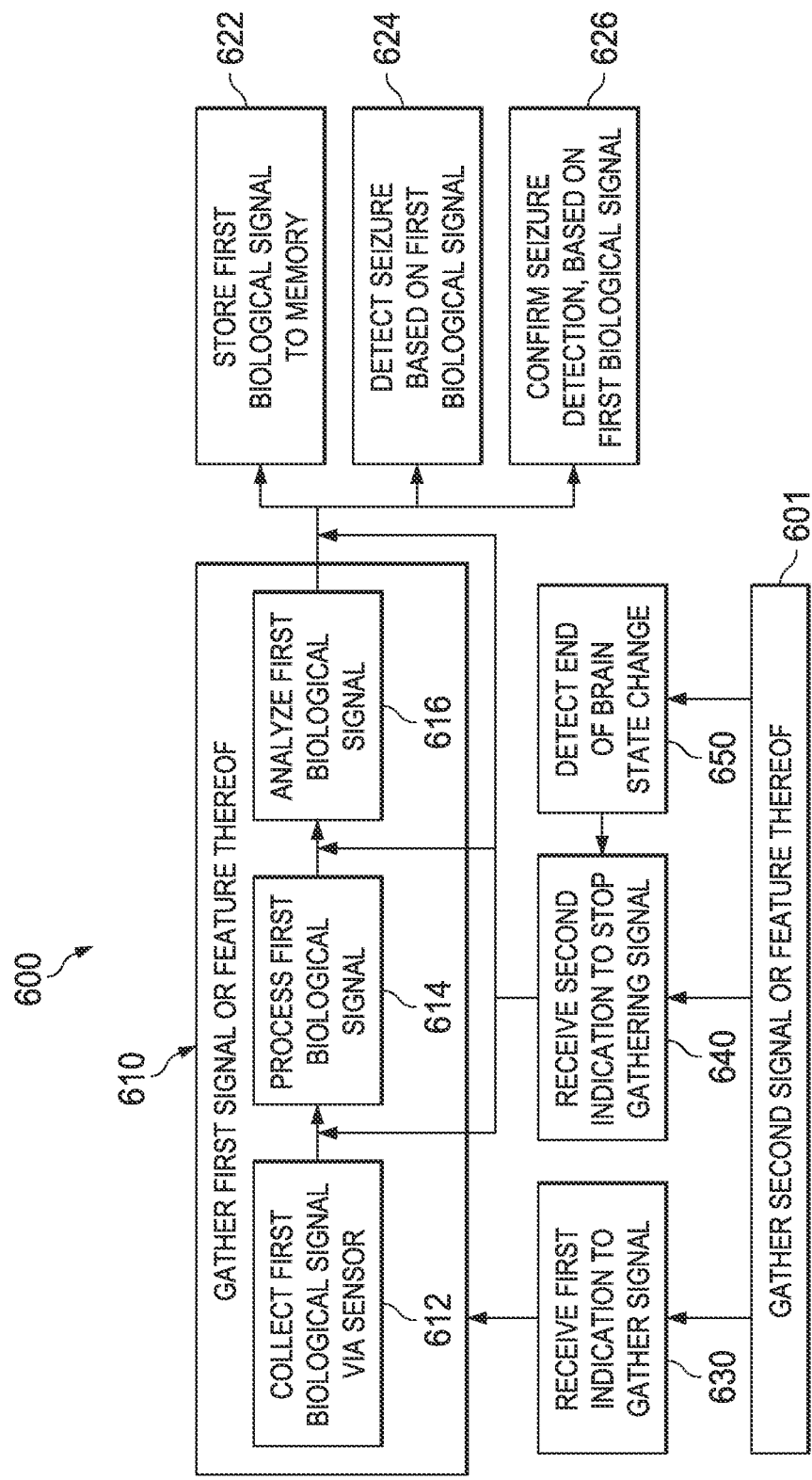
FIG. 6 shows a flowchart depiction of a method, according to some embodiments of the present disclosure.

Turning now to FIG. 6 flowchart representation of a method of performing a contingent acquisition, in accordance with another alternative embodiment, is illustrated. The method 600 may comprise receiving a first indication to gather a first biological signal or feature thereof from a patient (block 630). The first biological signal or feature thereof may be an autonomic signal or feature thereof, a neurologic signal or feature thereof, a metabolic signal or feature thereof, an endocrine signal or feature thereof, or a tissue stress marker signal or feature thereof. For example, the first biological signal or feature thereof may be an EKG signal or feature thereof, a kinetic signal or feature thereof, an electroencephalography (EEG) signal or feature thereof, an electrocorticography (ECoG) signal or feature thereof, a reaction time signal or feature thereof, an awareness signal or feature thereof, or a responsiveness signal or feature thereof.

The first indication may be based at least in part on at least one second biological signal or feature thereof from the patient gathered (block 601). The second biological signal or feature thereof may be an electrocardiography (EKG) signal or feature thereof or a kinetic signal or feature thereof. Alternatively or in addition, the first indication may be based at least in part on a first feature of the first signal or feature thereof (e.g., a value of the raw or a processed signal or feature thereof may be such that further analysis is desirable). For example, the second feature may be an R wave shape of an EKG signal, and the first, contingently gathered feature may be one of a T wave shape or of a Q-T interval. The first biological signal or feature thereof may be gathered (block 610), by which is meant that first biological signal or feature thereof is collected (block 612) via a sensor, processed (block 614), and analyzed (block 616). The first indication may activate one or more of elements 612-616, such that all three of elements 612-616 are performed. The first indication may be based at least in part on a detection of a brain state change onset, e.g., seizure onset, or entry into a period of increased seizure likelihood.

Thereafter, the method 600 may comprise receiving a second indication to stop gathering the first biological signal or feature thereof (block 640). The second indication may be based at least in part on at least one second biological signal or feature thereof gathered (block 601) from the patient. The second indication may relate to a detection of an end of a brain state change (block 650) or to the determination that the detection was false. This detection may be based on a second biological signal or feature thereof gathered (block 601). In response, the method 600 may comprise stopping gathering the first biological signal or feature thereof, which may be considered with reference to FIG. 6 as interruption of the flow from 612 to 614, 614 to 616, and/or 616 to one or more of 622-626.

The gathered first biological signal or feature thereof may be stored (block 622) to a memory (e.g., memory 217), used as at least a partial basis for a seizure detection (block 624), or used to confirm (block 626) a seizure detection based on other data, e.g., a continuously gathered second biological signal or feature thereof.

In some embodiments, the second biological signal or feature thereof may be selected from at least one of a cardiac signal or feature thereof, a kinetic signal or feature thereof, or a respiratory signal or feature thereof the first biological signal or feature thereof may be selected from at least one of the cardiac signal or feature thereof, the kinetic signal or feature thereof, and the respiratory signal or feature thereof, provided the first biological signal or feature thereof is different from the second biological signal or feature thereof the first indication may be based at least in part on the second biological signal or feature thereof and the first indication may be indicative of an epileptic event.

The first indication may be based at least in part on an occurrence of a seizure based on an EKG signal or feature thereof, and the second indication may be based at least in part on an end of the seizure based on the EKG signal or feature thereof. Alternatively or in addition, at least one of the first indication or the second indication may be based at least in part on at least one exosomatic signal or feature thereof. Examples of such exosomatic signal or feature thereof may include a time of day signal or feature thereof, a time of month signal or feature thereof, a luminance level signal or feature thereof, an acoustic noise level signal or feature thereof, a temperature signal or feature thereof, a barometric pressure signal or feature thereof, a signal or feature thereof indicative of a physical activity of the patient and when it was performed by the patient, a signal or feature thereof indicative of an attention level of the patient and when the patient was attentive, a signal or feature thereof indicative of a cognitive activity of the patient, the type of cognitive activity and when it was performed by the patient, a signal or feature thereof indicative of a time elapsed since the last seizure of the patient, the last seizure type or class, the last seizure severity of the patient, a signal or feature thereof indicative of a time elapsed since the delivery of a therapy to the patient, the type of therapy and its dose or parameters, the efficacy of the therapy, delivered to the patient, the adverse effects of the therapy and their type and severity, or a signal or feature thereof indicative of a time elapsed since the last caloric intake and its amount, a signal or feature thereof indicative of stress level and when it changes of the patient.

In some embodiments, the first and second biological signals or features thereof may be the same type of signal and/or same feature of a single signal collected at two different timescales, e.g., micro-, meso-, or macroscopic time scales.

In some embodiments, the second biological signal or feature thereof may be gathered continuously, and at some time, an event is detected based on changes of the signal or feature thereof; the detection triggers the gathering of the first biological signal or feature thereof; once the detected event terminates, gathering the second signal or feature thereof may be stopped, simultaneously with the detection or sometime later. For example, in the case of tonic-clonic seizures, accelerometer data may be continuously gathered, and if a seizure is detected from this data, the first indication may be to gather EEG or responsiveness data.

In some embodiments, the second biological signal or feature thereof is a cortical brain signal or feature thereof and the first biological signal or feature thereof is an electrocardiography (EKG) signal or feature thereof, a respiratory signal or feature thereof, a kinetic signal or feature thereof, a reaction time signal or feature thereof, an awareness signal or feature thereof, or a responsiveness signal or feature thereof.

In some embodiments, the present disclosure relates to a method, comprising sensing a first (e.g., continuously-gathered) biological signal or feature thereof with a first sensor; recording the first biological signal or feature thereof; sensing a second (e.g., contingently-gathered) biological signal or feature thereof with a second sensor; recording the second biological signal or feature thereof; buffering the second biological signal or feature thereof to a memory buffer; analyzing the first biological signal or feature thereof to determine at least one feature; detecting a brain state change based on the at least one feature of the first biological signal or feature thereof; initiating analysis of the second biological signal or feature thereof in response to detecting the brain state change; confirming or not confirming the brain state change based on the analysis of the second biological signal or feature thereof; detecting an end of the brain state change based on at least one of the first biological signal or feature thereof feature or the second biological signal or feature thereof; and stopping analysis of the second biological signal or feature thereof based on detecting the end of the seizure.

In some embodiments, the present disclosure relates to a method, comprising: sensing a first biological signal or feature thereof with a first sensor; analyzing the first biological signal or feature thereof to determine at least one feature; detecting a possible brain state change based on the at least one feature of the first biological signal or feature thereof, wherein the detecting comprises comparing the feature to a reference value; initiating at least one responsive action comprising analyzing a second biological signal or feature thereof in response to the detecting; and confirming or not confirming the possible brain state change based on the analyzing the second biological signal or feature thereof.

In some embodiments, the first biological signal or feature thereof is selected from a heart rate signal or feature thereof, an accelerometer signal or feature thereof, or both; and the second biological signal or feature thereof is selected from a heart rate signal or feature thereof, an accelerometer signal or feature thereof, a respiratory rate signal or feature thereof, an oxygen saturation signal or feature thereof, or two or more thereof, provided the second biological signal or feature thereof is different from the first biological signal or feature thereof. To be clear, the first and second biological signals may be the same as sensed and processed by components of the device, but with different first and second features thereof determined by body data module 175 and/or second body data module 180 (FIG. 1).

In some embodiments, three signals or features thereof may be considered, with two continuously gathered (e.g., heart rate, accelerometer) and used to initiate gathering of e.g., a respiratory signal or feature thereof (e.g., respiratory rate, blood oxygen saturation, etc.).

In some embodiments, when the patient is asleep, EKG only may be monitored, with a kinetic signal or feature thereof gathered contingently) in response to an increase in heart rate trigger analysis of buffered kinetic data, (e.g., the kinetic data is collected, processed, and stored in a short term buffer, but not analyzed, until an increase in heart rate occurs). Based on the analyzed kinetic data, a detection may be issued or not.

The method of this embodiment may further comprise detecting an end of the brain state change based on at least one of the first biological signal or feature thereof or the second biological signal or feature thereof; and stopping analysis of the second biological signal or feature thereof based on the detecting the end of the brain state change.

The responsive action referred to above may further comprise at least one of acquiring the second biological signal or feature thereof with a second sensor or buffering the second biological signal or feature thereof to a memory buffer.

The first biological signal or feature thereof may be selected from an electrocardiography (EKG) signal or feature thereof, a respiratory signal or feature thereof, an electroencephalography (EEG) signal or feature thereof, an electrocorticography (ECoG) signal or feature thereof, or a kinetic signal or feature thereof; and the second biological signal or feature thereof may be selected from a reaction time, an awareness signal or feature thereof, or a responsiveness signal or feature thereof.

The first signal or feature thereof may be used to detect a seizure and the second signal or feature thereof may be used to classify the seizure. For example, the second signal or feature thereof may be used to classify the seizure as complex partial in response to the patient being unaware or unresponsive. Similar examples exist for other seizure types, e.g., tonic-clonic seizures, complex partial hypermotoric or hypomotoric seizures, etc. For example, complex partial hypermotoric seizures have loss of responsiveness and large spikes in accelerometer data.

In some embodiments, threshold(s) and/or duration(s) of seizure detection algorithms, and/or issuing a warning regarding and/or logging the outputs of the seizure detection algorithms, may be based on results of contingent gathering, e.g., if heart rate-based seizure detection requires the heart rate to be above a seizure threshold for 5 sec, and accelerometer indication of a seizure is temporally correlated with a heart rate indication, then duration can be lowered. For example, the duration can be lowered to the time of accelerometer indication.

Figure 7:
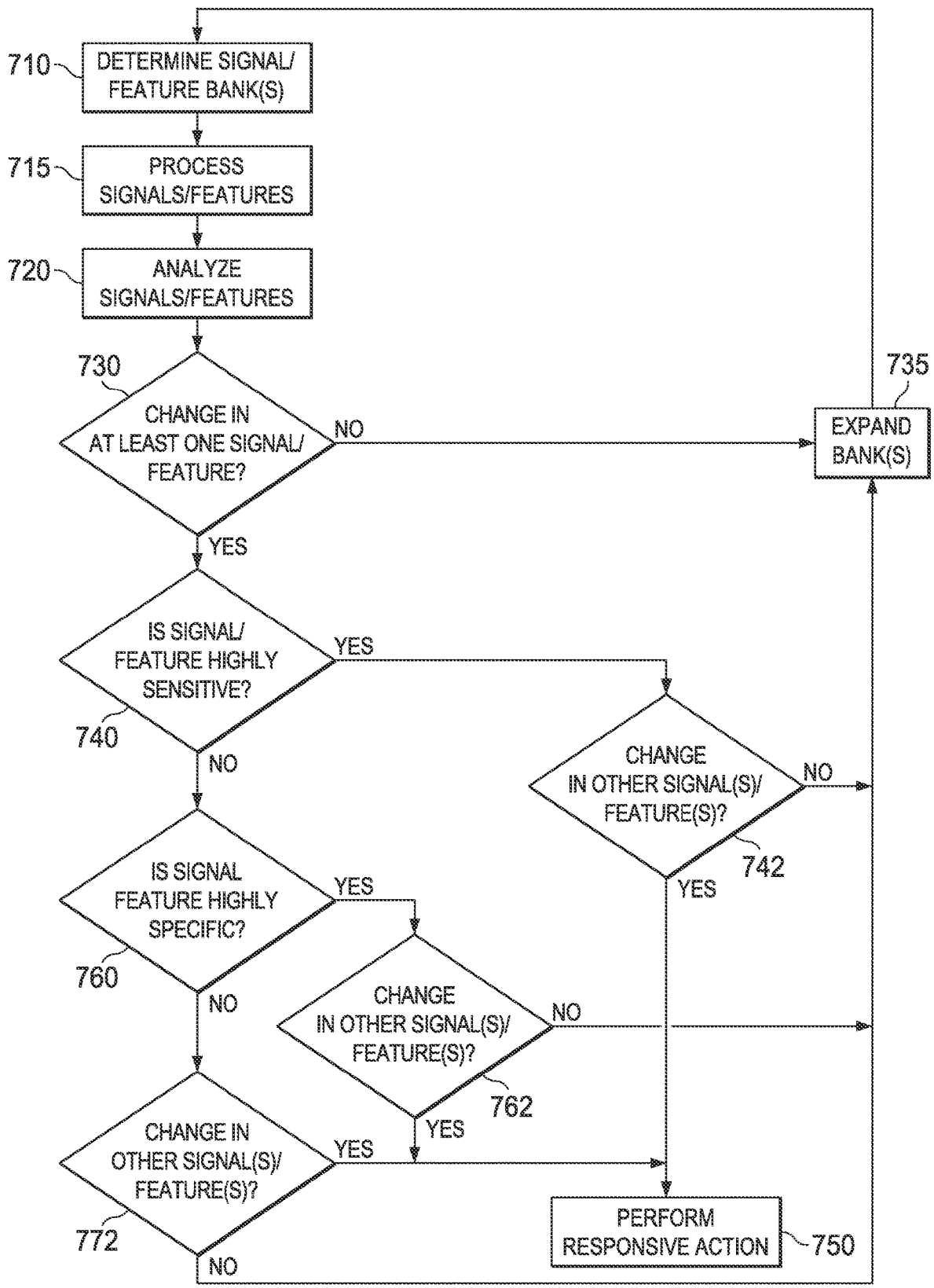
FIG. 7 shows a flowchart depiction of a method, according to some embodiments of the present disclosure.

FIG. 7 presents a flowchart depiction of a method 700, according to some embodiments of the present disclosure. The method 700 may allow qualitative or quantitative ranking of the sensitivity, specificity, or both of one or more signals or features thereof.

One or more banks of signals and/or features may be determined (at 710). The signals/features may be HR, HRV, EKG morphology, respiratory rate (RR), respiratory rate variability (RRV), EEG, EEG power variability at one or more frequency bands, etc. One or more of these signals/features may be processed (at 715) and analyzed (at 720).

Whether or not a change in at least one signal/feature has occurred may be determined (at 730). If no change has occurred, it may be desirable to expand the bank(s) of features (at 735). On the other hand, if a change has occurred, it may be indicative of a pathological state in the patient. It may be desirable to confirm the occurrence of the pathological state, depending on the sensitivity and/or specificity of the signal/feature for indicating the occurrence of the pathological state.

In the depicted embodiment, if a change occurred (as determined at 730), then it may be determined (at 740) if the signal/feature is highly sensitive to the pathological state of interest, e.g., that it has a sensitivity that places it in the top decile of signals/features. (By "change" is meant a significant deviation of a signal/feature value from a measure of central tendency thereof). If the signal/feature is determined to not be highly sensitive, then it may be determined (at 760) if the signal/feature is highly specific to the pathological state, e.g., that it has a specificity that places it in the top decile of signals/features. If the signal/feature is determined to be neither highly sensitive nor highly specific, then it may be considered as being an intermediate signal/feature. Signals/features may be also selected for speed of detection, that is, they are the first to change when a transition from a non-pathological to a pathological state occurs.

Whether the signal/feature is highly sensitive, highly specific, or intermediate, upon a determination of its sensitivity/specificity (e.g., at 740 or 760), then whether a change in (an)other signal(s)/feature(s) occurred may be determined (e.g., at 742, 762, or for intermediate signals/features, 772). The other signal(s)/feature(s) may be selected such that a change in it/them may confirm or complement a change observed (at 730) in the main signal/feature of interest. For example, if the main signal/feature of interest is highly sensitive, then the other signal(s)/feature(s) considered (at 742) may be one(s) that are highly specific so as to decrease the probability of false positive detections. Similar considerations apply to the change determinations at 762 and 772.

If a change in the other signal(s)/feature(s) is determined to have occurred (at 742, 762, or 772), then a responsive action may be performed (at 750). The responsive action may comprise (re)determining the main signal/feature's sensitivity or specificity, repeating the process (by returning to determining the signal/feature bank(s) at 710), or the like. Other responsive actions may include but are not limited to issuing a detection, a warning, logging data associated with the detection, or delivering a therapy.

As should be apparent to the person of ordinary skill in the art, an explicit determination that the main signal/feature of interest is an intermediate signal/feature may be made, and/or 740, 760, and any explicit determination of an intermediate signal/feature may be made in any order.

Figure 8:
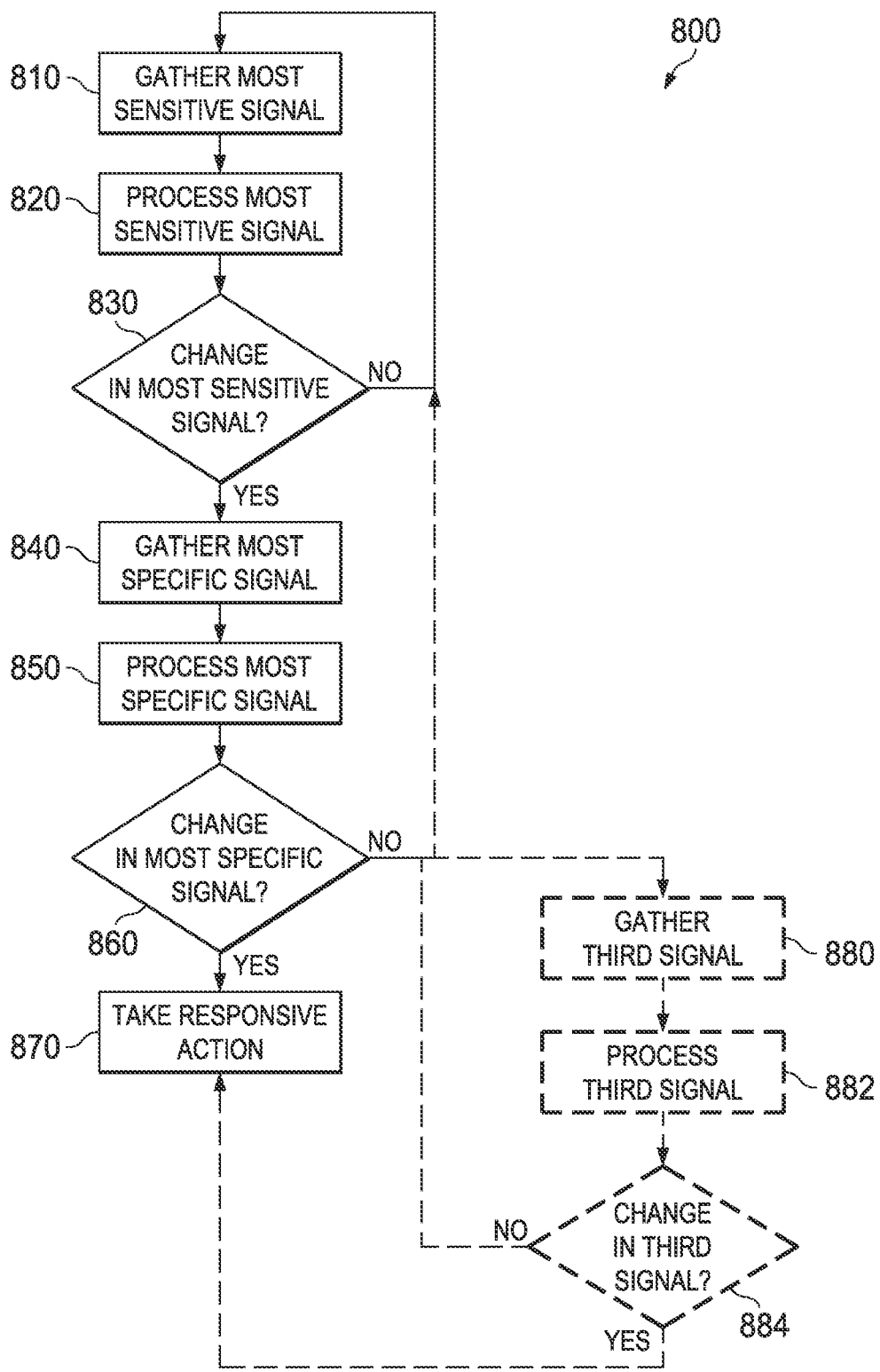
FIG. 8 shows a flowchart depiction of a method, according to some embodiments of the present disclosure.

FIG. 8 provides a flowchart depiction of a method 800 according to some embodiments of the present disclosure. Given a plurality of signals that may be gathered from body data of a patient, the most sensitive signal (i.e., the signal of the plurality which has the highest sensitivity for detecting a pathological state of interest) may be gathered (at 810) and processed (or analyzed) (at 820). Whether a change in the most sensitive signal has occurred may be determined (at 830).

If the most sensitive signal has not changed, the method may return to gathering other sensitive signals (at 810). On the other hand, if the most sensitive signal has changed, then the most specific signal may be gathered (at 840) and processed (or analyzed) (at 850). Whether a change in the most specific signal has occurred may be determined (at 860).

If a change in the most specific signal has occurred, then, in light of this change and the change in the most sensitive signal (previously determined at 830), i.e., that both signals agree that a pathological state occurred, then a responsive action may be taken (at 870). The responsive action may comprise one or more of issuing a detection of the pathological state, warning the patient or a caregiver of the detected pathological state, providing a therapy for the pathological state, logging an occurrence of the pathological state, processing or analyzing body data expected to be informative about the pathological state, or ceasing processing or analysis of body data not/no longer expected to be informative about the pathological state, among others. If no change occurred in the most specific signal, then the method may return to gathering the most sensitive signal (at 810), or it may optionally proceed to gather (at 880) and process or analyze (at 882) a third signal. Whether a change in the third signal has occurred may be determined (at 884).

If a change in the third signal has occurred, then, in light of this change and the changes in the most sensitive and most specific signals (previously determined at 830 and 860), i.e., that the third signal confirms an occurrence of a pathological state tentatively identified by changes in the most sensitive and most specific signals, then a responsive action may be taken (at 870), as described above. This approach may be taken when certainty about the occurrence of a pathologic state is advisable to issue a warning (to avoid undue unwarranted distress to the patient and adoption of unnecessary precautions if a false detection is issued) or delivery of a therapy that while efficacious in preventing or blocking the pathological state may cause certain unsafe or intolerable side effects.

If no change occurred in the third signal, then the method may return to gathering the most sensitive signal (at 810).

As the person of ordinary skill in the art will readily understand, the order of elements 810-830 and 840-860 may differ, i.e., the most specific signal may be gathered first and the most sensitive, second.

Figure 9:
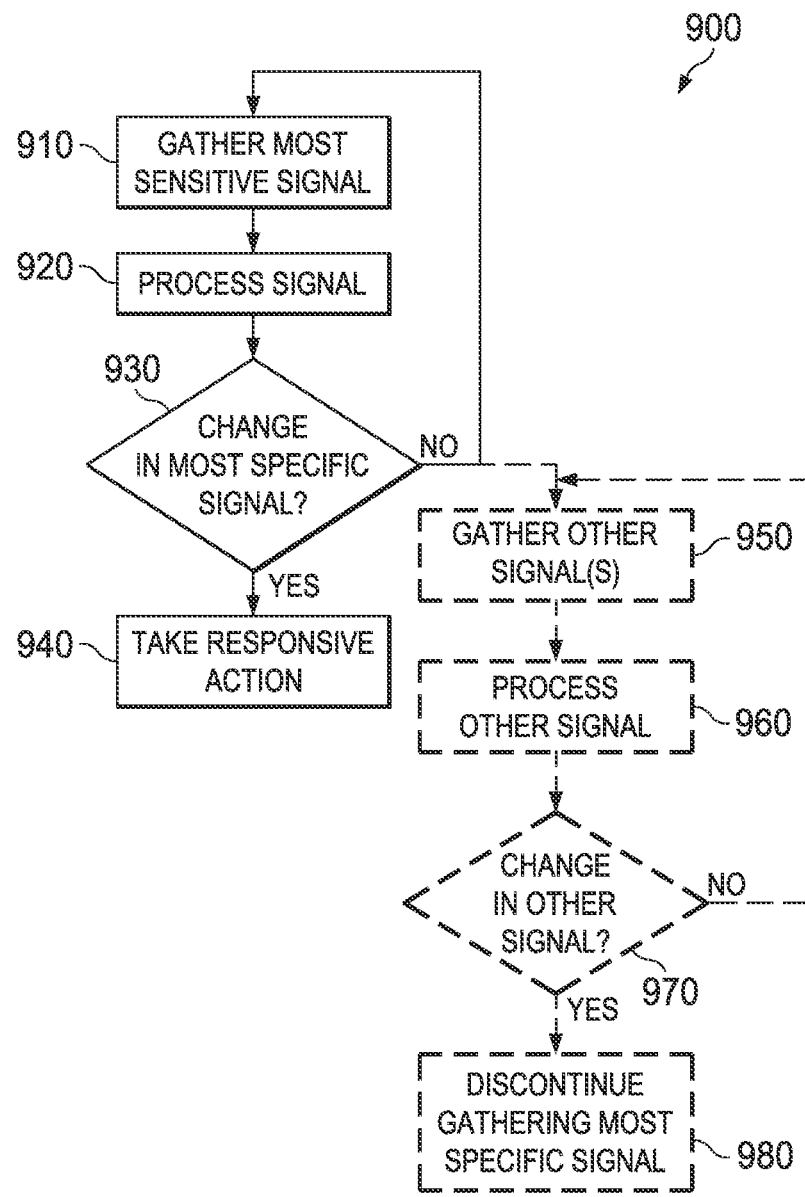
FIG. 9 shows a flowchart depiction of a method, according to some embodiments of the present disclosure.

FIG. 9 presents a flowchart depiction of a method 900 according to some embodiments of the present disclosure. The method 900 may allow detection of a pathological state in a patient in a highly specific manner. A most specific signal may be gathered (at 910) and processed (or analyzed) (at 920), and whether a change in the most specific signal occurred may be determined (at 930).

If a change in the most specific signal has occurred, i.e., a highly specific indication has arisen that the patient is in a pathological state then a responsive action may be taken (at 940). The responsive action may comprise one or more of those described elsewhere herein. Choice of a "most" specific signal may simplify the process of detection of pathological states without compromising accuracy.

If the most specific signal has not undergone a change, then the method may return to gathering the most specific signal (at 910), or one or more other signals may be gathered (at 950), processed (or analyzed) (at 960), and whether a change in the other signal(s) has occurred may be determined (at 930). A lack of change in the other signal may indicate that yet another signal may be gathered (at 950), etc., or that the method may return to gathering the most specific signal (at 910). An observed change in the other signal (at 970) may render it desirable to discontinue gathering the most specific signal (e.g., the "most specific" signal may turn out to have an undesirably low sensitivity, and gathering of a different signal may be desirable. The method may include the step of discontinue gathering most specific signal (at 980).

In some embodiments, the present disclosure relates to a method, comprising: gathering a first biological signal or feature thereof from a patient; receiving an indication to gather a second biological signal or feature thereof from the patient; gathering the second biological signal or feature thereof; determining at least one of a sensitivity, a specificity, or a speed of detection of a pathological state in the patient from both the first biological signal or feature thereof and the second biological signal or feature thereof; continuing gathering of the biological signal or feature thereof having a better sensitivity of detection, a better specificity of detection, or a better speed of detection; and stopping gathering of the biological signal or feature thereof having a poorer sensitivity of detection, a poorer specificity of detection, or a poorer speed of detection.

The methods depicted in FIGS. 4-9 and/or described above may be governed by instructions that are stored in a non-transitory computer readable storage medium and that are executed by, e.g., a processor 217 of the medical device 200. Each of the operations shown in FIGS. 4-9 and/or described above may correspond to instructions stored in a non-transitory computer memory or computer readable storage medium. In various embodiments, the non-transitory computer readable storage medium includes a magnetic or optical disk storage device, solid state storage devices such as flash memory, or other non-volatile memory device or devices. The computer readable instructions stored on the non-transitory computer readable storage medium may be in source code, assembly language code, object code, or other instruction format that is interpreted and/or executable by one or more processors.

In some embodiments, the present disclosure may relate to one or more of the following numbered paragraphs:

101. A non-transitory computer readable program storage unit encoded with instructions that, when executed by a computer, perform a method, comprising:
receiving a first indication to gather a first biological signal or feature thereof from a patient;
gathering said first biological signal or feature thereof;
receiving a second indication to stop gathering said first biological signal or feature thereof, wherein the second indication relates to a detection of an end of a brain state change; and
stopping gathering said first biological signal or feature thereof.

102. The non-transitory computer readable program storage unit of numbered paragraph 101, wherein at least one of said first indication or said second indication is based at least in part on at least one second biological signal or feature thereof from said patient.

103. The non-transitory computer readable program storage unit of numbered paragraph 101, wherein said first indication is based at least in part on a first feature of said first signal or feature thereof, and said second indication is based at least in part on a first feature of a second biological signal or feature thereof.

104. The non-transitory computer readable program storage unit of numbered paragraph 101, wherein the first signal or feature thereof is selected from an autonomic signal or feature thereof, a neurologic signal or feature thereof, a metabolic signal or feature thereof, an endocrine signal or feature thereof, or a tissue stress marker signal or feature thereof.

105. The non-transitory computer readable program storage unit of numbered paragraph 102, wherein the second biological signal or feature thereof is selected from an electrocardiography (EKG) signal or feature thereof or a kinetic signal or feature thereof, and the first biological signal or feature thereof is selected from the other of said EKG signal or feature thereof and kinetic signal or feature thereof, an electroencephalography (EEG) signal or feature thereof, an electrocorticography (ECoG) signal or feature thereof, a reaction time signal or feature thereof, an awareness signal or feature thereof, or a responsiveness signal or feature thereof.

106. The non-transitory computer readable program storage unit of numbered paragraph 102, wherein said second biological signal or feature thereof is selected from at least one of a cardiac signal or feature thereof, a kinetic signal or feature thereof, or a respiratory signal or feature thereof; said first biological signal or feature thereof is selected from at least one of said cardiac signal or feature thereof, said kinetic signal or feature thereof, and said respiratory signal or feature thereof, provided said first biological signal or feature thereof is different from said second biological signal or feature thereof; said first indication is based at least in part on said second biological signal or feature thereof; and said first indication is indicative of an epileptic event.

107. The non-transitory computer readable program storage unit of numbered paragraph 102, wherein the second biological signal or feature thereof is a cortical brain signal or feature thereof and the first biological signal or feature thereof is an electrocardiography (EKG) signal or feature thereof, a respiratory signal or feature thereof, a kinetic signal or feature thereof, a reaction time signal or feature thereof, an awareness signal or feature thereof, or a responsiveness signal or feature thereof.

108. The non-transitory computer readable program storage unit of numbered paragraph 105, wherein said first indication is an indication of an occurrence of a seizure based on said EKG signal or feature thereof, and said second indication is of an end of said seizure based on said EKG signal or feature thereof.

109. The non-transitory computer readable program storage unit of numbered paragraph 101, wherein at least one of said first indication or said second indication is based at least in part on at least one exosomatic signal or feature thereof.

110. The non-transitory computer readable program storage unit of numbered paragraph 105, wherein the at least one exosomatic signal or feature thereof is a time of day signal or feature thereof, a time of month signal or feature thereof, a luminance level signal or feature thereof, an acoustic noise level signal or feature thereof, a temperature signal or feature thereof, a barometric pressure signal or feature thereof, a signal or feature thereof indicative of a physical activity of said patient and when it was performed by said patient, a signal or feature thereof indicative of an attention level of said patient and when said patient was attentive, a signal or feature thereof indicative of a cognitive activity of said patient, the type of cognitive activity and when it was performed by said patient, a signal or feature thereof indicative of a time elapsed since the last seizure of said patient, the last seizure type or class, the last seizure severity of said patient, a signal or feature thereof indicative of a time elapsed since the delivery of a therapy to said patient, the type of therapy and its dose or parameters, the efficacy of said therapy, delivered to said patient, the adverse effects of said therapy and their type and severity, or a signal or feature thereof indicative of a time elapsed since the last caloric intake and its amount, a signal or feature thereof indicative of stress level and when it changes of said patient.

201. A medical device system, comprising:
a first sensor configured to sense a first biological signal or feature thereof from a patient;
a signal or feature thereof recorder module configured to record said first biological signal or feature thereof;
a signal or feature thereof analysis module configured to analyze said first biological signal or feature thereof;
a controller configured to generate a first indication based on a second biological signal or feature thereof to activate at least one of said first sensor, said signal or feature thereof recorder module, or said signal or feature thereof analysis module, such that all of said first sensor, said signal or feature thereof recorder module, and said signal or feature thereof analysis module are activated and to generate a second indication based on said second biological signal or feature thereof to deactivate at least one of said first sensor, said signal or feature thereof recorder module, or said signal or feature thereof analysis module; and
a memory configured to store at least said first analyzed biological signal or feature thereof.

202. The medical device system of numbered paragraph 201, further comprising:
a brain state change detection module configured to detect a brain state change, based at least in part on said first biological signal or feature thereof.

203. The medical device system of numbered paragraph 201, wherein said brain state change is an epileptic seizure.

204. The medical device system of numbered paragraph 201, wherein said first indication is based on a seizure event onset determined from said second biological signal or feature thereof, and said second indication is based on a seizure event end determined from said second biological signal or feature thereof.

205. The medical device system of numbered paragraph 201, wherein said first biological signal or feature thereof is an electroencephalography (EEG) signal or feature thereof, an electrocorticography (ECoG) signal or feature thereof, a kinetic signal or feature thereof, a reaction time signal or feature thereof, an awareness signal or feature thereof, or a responsiveness signal or feature thereof.

206. The medical device system of numbered paragraph 201, wherein said signal or feature thereof analysis module is configured to determine a first feature of said first biological signal or feature thereof, wherein the first feature is one of power in certain frequency band, a rhythmicity index, a waveform morphology, a synchronization level, a direction of a movement, an amplitude of a movement or an acceleration of a movement.

207. The medical device system of numbered paragraph 201, further comprising:
a second sensor configured to sense a second biological signal or feature thereof from said patient;
wherein said controller is configured to generate at least one of said first indication or said second indication based at least in part on said second biological signal or feature thereof.

208. The medical device system of numbered paragraph 207, wherein said second biological signal or feature thereof is an electrocardiography (EKG) signal or feature thereof.

209. The medical device system of numbered paragraph 201, wherein said first biological signal or feature thereof is an electrocardiography (EKG) signal or feature thereof and said signal or feature thereof analysis module is configured to determine a first feature of said first biological signal or feature thereof, wherein said first feature is one of heart rate, heart rate variability, EKG morphology, heart rhythm, or Q-T interval.

210. The medical device system of numbered paragraph 201, wherein said controller is configured to generate at least one of said first indication or said second indication based at least in part on at least one exosomatic signal or feature thereof.

211. The medical device system of numbered paragraph 210, wherein the at least one exosomatic signal or feature thereof is a time of day signal or feature thereof, a time of month signal or feature thereof, a luminance level signal or feature thereof, an acoustic noise level signal or feature thereof, a temperature signal or feature thereof, a barometric pressure signal or feature thereof, a signal or feature thereof indicative of a physical activity of said patient and when it was performed by said patient, a signal or feature thereof indicative of an attention level of said patient and when said patient was attentive, a signal or feature thereof indicative of a cognitive activity of said patient, the type of cognitive activity and when it was performed by said patient, a signal or feature thereof indicative of a time elapsed since the last seizure of said patient, the last seizure type or class, the last seizure severity of said patient, a signal or feature thereof indicative of a time elapsed since the delivery of a therapy to said patient, the type of therapy and its dose or parameters, the efficacy of said therapy, delivered to said patient, the adverse effects of said therapy and their type and severity, or a signal or feature thereof indicative of a time elapsed since the last caloric intake and its amount, a signal or feature thereof indicative of stress level and when it changes of said patient.

What is claimed:

1. A method, comprising:
    receiving via a medical device a sentinel biological signal from a patient;
    analyzing via the medical device data relating to the sentinel biological signal;
    determining via the medical device whether a seizure is about to occur based upon the analyzing;
    acquiring via the medical device a non-sentinel signal solely in response to the determination that the seizure is about to occur, wherein the non-sentinel signal and the sentinel biological signal are different signal types;
    analyzing via the medical device data relating to the non-sentinel signal acquired solely in response to the determination that the seizure is about to occur;
    confirming via the medical device the seizure based upon the analyzing of the data relating to the non-sentinel signal;
    performing via the medical device a responsive action in response to confirming the seizure, wherein the responsive action is an electrical therapy delivery;
    wherein analyzing data relating to the sentinel biological signal comprises:
        extracting data or features from the sentinel biological signal;
        comparing at least one feature of the sentinel biological signal to a first reference feature; and
        determining whether the comparing of the at least one feature of the sentinel biological signal to the first reference feature is indicative of a seizure data; and
    wherein analyzing data or the features relating to the non-sentinel signal comprises:
        extracting data or features from the non-sentinel signal;
        comparing at least one feature of the non-sentinel signal to a second reference feature;
        determining whether the comparing of the at least one feature of non-sentinel signal to the second reference feature confirms an occurrence of an epileptic event; and
        logging data to a memory capable of logging a predicted time and date for a predicted seizure where the predicted seizure is based on the determining via the medical device whether the seizure is about to occur based upon the analyzing data relating to the sentinel biological signal;
        wherein the acquisition of the non-sentinel signal ceases in response to the determination that an occurrence of the seizure has been confirmed and acquisition of the non-sentinel signal is resumed upon a second determination that a second seizure is about to occur;
        wherein the feature of the sentinel biological signal is heart rate and the non-sentinel signal is heart rate variability.

2. The method of claim 1, wherein the seizure is an epileptic seizure.

3. The method of claim 1, wherein responsive action further comprises issuing a warning to at least one of the patient, a caregiver or a healthcare provider.

4. The method of claim 1, wherein the determination that the seizure is about to occur refers to an onset of the epileptic event.

5. A method, comprising:
    sensing via a medical device a sentinel biological signal or feature thereof with a first sensor or electrode;
    analyzing via the medical device the sentinel biological signal or feature thereof to determine at least one feature;
    detecting via the medical device a probable seizure based on the at least one feature of the sentinel biological signal or feature thereof, wherein the detecting comprises comparing the feature to a reference value;
    initiating via the medical device at least one responsive action comprising acquiring and analyzing a non-sentinel signal or feature thereof in response to the probable seizure;
    confirming via the medical device the probable seizure based on the analyzing the non-sentinel signal or feature thereof, wherein the non-sentinel signal and the sentinel biological signal are different signal types;
    wherein analyzing data relating to the sentinel biological signal comprises:
        extracting data or features from the sentinel biological signal;
        comparing at least one feature of the sentinel biological signal to a first reference feature; and
        determining whether the comparing of the at least one feature of the sentinel biological signal to the first reference feature is indicative of a seizure data; and
    wherein analyzing data or the features relating to the non-sentinel signal comprises:
        extracting data or features from the non-sentinel signal;
        comparing at least one feature of the non-sentinel signal to a second reference feature; and
        determining whether the comparing of the at least one feature of non-sentinel signal to the second reference feature confirms an occurrence of an epileptic event; and
    delivering an electrical therapy to a vagus nerve based on the occurrence of the epileptic event; and
    logging data to a memory capable of logging a predicted time and date for a predicted seizure where the predicted seizure is based on the detecting via the medical device the probable seizure based on the at least one feature of the sentinel biological signal or feature thereof;
    wherein the feature of the sentinel biological signal is heart rate and the non-sentinel signal is heart rate variability.

6. The method of claim 5, further comprising:
    confirming the epileptic event based on the non-sentinel signal or feature thereof;
    confirming an end of the epileptic event based on a value returning to a baseline number; and
    stopping acquiring or analyzing of the non-sentinel signal or feature thereof based on the detection of the end of the epileptic event.

7. The method of claim 5, wherein the responsive action further comprises at least one of acquiring the non-sentinel signal or feature thereof with a second sensor or buffering the non-sentinel signal or feature thereof to a memory buffer.

* * * * *